United States Patent
Mahmud et al.

(10) Patent No.: US 6,600,078 B1
(45) Date of Patent: Jul. 29, 2003

(54) LIQUID PHASE CATALYTIC HYDROGENATION PROCESS TO CONVERT ALDEHYDES TO THE CORRESPONDING ALCOHOLS

(75) Inventors: Meftahuddin Mahmud, Riyadh (SA); Ahmad Kamal Faizi, Riyadh (SA); Vidyasagar Anchoori, Riyadh (SA); Abdullah Al-Qahtani, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 10/110,904

(22) PCT Filed: Oct. 18, 2000

(86) PCT No.: PCT/IB00/01503

§ 371 (c)(1),
(2), (4) Date: Aug. 12, 2002

(87) PCT Pub. No.: WO01/28964

PCT Pub. Date: Apr. 26, 2001

(30) Foreign Application Priority Data

Oct. 20, 1999 (EP) .............................. 99121002

(51) Int. Cl.$^7$ .............................. C07C 39/10
(52) U.S. Cl. .................. 568/764; 546/344; 549/503; 568/772; 568/814; 568/862; 568/881
(58) Field of Search ................ 568/772, 862, 568/764, 814, 881; 549/503; 546/344

(56) References Cited

U.S. PATENT DOCUMENTS

| 4,021,496 A | 5/1977 | Wright |
| 4,250,337 A | 2/1981 | zur Hausen et al. |
| 4,393,251 A * | 7/1983 | Broecker |
| 4,855,515 A | 8/1989 | Morris et al. |
| 5,146,012 A | 9/1992 | Salek et al. |
| 5,155,086 A * | 10/1992 | Thakur |
| 5,302,569 A | 4/1994 | Horn |
| 5,334,779 A | 8/1994 | Kuo |

FOREIGN PATENT DOCUMENTS

| EP | 0 008 767 A1 | 3/1980 |
| EP | 0 424 069 A1 | 4/1991 |
| EP | 0 484 800 A2 | 5/1992 |
| EP | 0 528 305 A2 | 2/1993 |

* cited by examiner

*Primary Examiner*—Michael L. Shippen
(74) *Attorney, Agent, or Firm*—Kramer Levin; Naftalis & Frankel

(57) ABSTRACT

A heterogeneous liquid-phase process for the hydrogenation of aldehydes of Formula (I) and (III) to the corresponding alcohols of Formula (II) and (IV) which process comprises contacting alcoholic or aqueous-alcoholic solution of aldehydes and hydrogen gas with a catalyst comprising a reduced mixture of CuO and ZnO in presence of a metal of group IIIA of the Periodic Table, such as aluminium, as a promoter at a temperature of between about 110° and 180° C. and a pressure of between about 20 and 500 psig.

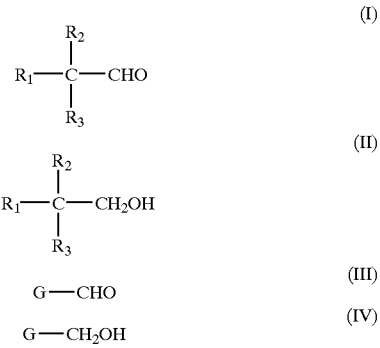

28 Claims, No Drawings

LIQUID PHASE CATALYTIC HYDROGENATION PROCESS TO CONVERT ALDEHYDES TO THE CORRESPONDING ALCOHOLS

BACKGROUND OF THE INVENTION

1. Field of the Invention

This invention relates generally to a heterogeneous process for the liquid phase hydrogenation of aldehydes to the corresponding alcohols using reduced form of CuO/ZnO catalyst in the presence of a metal from Group IIIA of the Periodic Table such as aluminium. More particularly, this invention relates to the hydrogenation of hydroxypivalaldehyde to neopentylglycol.

2. Description of the Prior Art

Aldehydes and corresponding primary alcohols are two general classes of organic compounds. There are several methods known in any textbook of organic chemistry and in patent literature for the conversion of aldehydes to the corresponding primary alcohols, such as chemical reduction methods using alkali or alkaline earth metal-derived borohydrides or aluminium hydrides and metal catalyzed-hydrogenation. Chemical reduction processes are seldom commercially viable. Usefulness of metal-catalytic processes is determined by conversion of aldehydes especially in presence of harmful impurities such as amines or other bases, selectivity of primary alcohol products, reaction conditions such as temperature and pressure, and even more importantly environmental issues caused by the metal catalysts.

Some of the conventionally used metal catalysts, although applied specifically for hydrogenation of hydroxypivaldehyde for making neopentyl glycol, may be equally effective to hydrogenate any aldehyde to the corresponding primary alcohol. This method is disclosed in Japanese Patent Publication Nos. 33169/1974,/ 17568/1678, U.S. Pat. Nos. 1,048,530, 1,219,162, 3,920,760, 4,021,496, West German Patent No. 1,014,089, and European Patent Nos. 44,421, 44,444. In these patents, Raney nickel, Ni—Cr, Cu—Zn, Cu—Al, Cu—Cr and Cr—Ba catalysts are disclosed as catalysts for use in such hydrogenation reaction.

These conventional catalysts suffer from problems in that the catalytic activity in insufficient and thus the reaction must be carried out under high pressure conditions and that catalytic activity can not be maintained at a high level for a long period of time since it is decreased under the influences of small amounts impurities contained in the starting materials, thee aldehydes. In the case of the Raney nickel catalyst, various problems arise; for example, preparation and handling of the catalyst are not easy, catalytic activity is insufficient and furthermore it can not be maintained for a long time, and since the catalyst is used in a slurry form, the process inevitably becomes complicated.

The followings are some of the prior arts related to our invention. For example, J. S. Salek et.al., in U.S. Pat. No. 5,146,012 (assigned to Aristech Chem) have disclosed the use of copper chromite for hydrogenation of hydroxypivalaldehyde to neopentylglycol. Chromium-based catalysts, in general, are now becoming environmentally unacceptable.

British Pat. Nos. 1,017,618 and 1,048,530, describe the hydrogenation of hydroxypivalaldehyde to neopentyl glycol in the presence of copper/chromium oxide catalyst. However, this catalyst system gave poor selectivity of neopentyl glycol due to formation of some by-products.

In other prior arts, such as in U.S. Pat. No. 4,250,337 (assigned to Chemische Werke Huls Aktiengesellschaft, Germany) and in U.S. Pat. No. 4,855,515 (assigned to Eastman Kodak, USA) barium and manganese-promoted copper chromite respectively have been disclosed as hydrogenation catalyst. The reactions were carried out at 500–1000 psig, and at a temperature of 170–220° C. It is now known that chromium-based catalyst pose health risks. Moreover, at high temperatures, this catalyst can decompose the starting material hydroxypivaldehyde adversely affecting the quality of final product and decreasing its yield.

German Published Application DAS No. 1,957,551 discloses the use of cobalt and nickel based catalysts in the hydrogenation of hydroxypivalaldehyde to neopentyl glycol, at high hydrogenation temperatures. Still another prior art WO 98/17614 (assigned to LG Chemicals, Korea) has described the use of Raney nickel in the hydrogenation of hydroxypivalaldehyde at low temperatures. But, these transition metal catalysts are deactivated by the presence of trace amounts of formaldehyde, or isobutyraldehyde, or trialkyl amine, which are present as impurities in the starting material hydroxypivalaldehyde. Besides, due to their pyrophoric nature these catalysts can not be easily prepared and handled as they have to be used in the slurry form.

T. Ninomiya et.al. have described in U.S. Pat. No. 4,933,473 (assigned to Mitsubishi Gas, Japan) the usage of a trimetallic (Pt/Ru/W) catalyst system for hydrogenation of hydroxypivalaldehyde. Although a 100% conversion of starting aldehyde and 100% selectivity of product are achieved at low reaction temperatures like 120° C., and at low pressure of 140–150 psig. a commercialization of this catalyst system is unlikely due to high cost of these metals.

In one of the closest prior art, EP 484800, the use of CuO/ZnO in presence of ZrO is disclosed for hydrogenation of hydroxypivaldeyhde wherein the use of 25% percent equivalent (by weight) of the catalyst makes the process commercially unattractive.

The closest prior art appears to be European Patent Application EP 008767 (assigned to Union Carbide) wherein CuO/ZnO catalyst system has been disclosed for reducing aldehydes to the corresponding primary alcohols. However, this process is severely limited only to a vapor-phase process, it did not become quite obvious to them if this catalyst system would have worked equally well in a liquid phase process, in general, with all other kinds of aldehydes such aromatic/or heterocyclic/or other branched aliphatic aldehydes.

Therefore, one of the objectives of the present invention is to overcome the difficulties and disadvantages encountered in the prior arts by providing a liquid-phase hydrogenation process utilizing a novel catalyst system comprising reduced form of CuO/ZnO in the presence of aluminium, a promoter for superior performance.

SUMMARY OF THE INVENTION

The present invention provides a liquid-phase general catalytic hydrogenation process for aldehydes to the corresponding primary alcohols. The catalyst system comprises of copper oxide and zinc oxide with aluminium as a promoter. The process of this invention, although general, is particularly useful for the hydrogenation of hydroxypivalaldehyde to neopentyl glycol. This process allows the hydrogenation to be carried out at moderate pressures such as 400–500 psig providing 100% conversion of aldehyde with 100% selectivity of the desired alcohol.

ADVANTAGEOUS EFFECT OF THE INVENTION

The efficiency of the catalyst is retained even in the presence of deleterious impurities like trialkyl amine and quaternary ammonium hydroxide that may have been carried over to certain crude aldehyde products during their synthesis.

This invention is particularly useful for making neopentyl glycol from hydroxypivaldehyde in 100% selectivity as this aldehyde does not decompose under hydrogenation conditions of this invention.

The particular product, namely 2,2-dimethyl-1,3-dihydroxypropane (neopentyl glycol) of the process of the present invention is a valuable starting material for the manufacture of lubricants, plastics, surface coatings and synthetic resins, for example corresponding polyesters.

The process of the invention may be a continuous process or a batch process.

DETAILED DESCRIPTION OF THE INVENTION

The following is the basic reaction of the present invention:

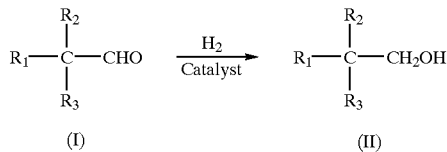

where, $R_1$, $R_2$, and $R_3$ individually could be straight chain or branched alkyl group containing 1–18 carbon atoms, or straight alkyl group containing 1–18 carbon atoms intervening with one or more hetero atoms such as oxygen, nitrogen, sulfur and phosphorus atoms, or alicyclic rings containing three or more carbon atoms when the ring(s) may or may not contain hetero atoms, or $R_1$, $R_2$, and $R_3$ together or alternately may form an alicyclic or aromatic rings, or any one or more of the R groups may contain one or more primary or secondary or tertiary alcohol group(s).

Also,

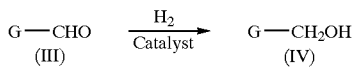

where, G group can be a substituted or unsubstituted and fused or isolated aromatic or heterocyclic rings. For example, it can be a p-hydroxybenzyl group or a pyridinyl or furyl group.

The catalyst may be prepared by any of the methods known in the art of forming a composite of copper oxide and zinc oxide. The catalyst may be prepared by fixing the separate oxides, by co-precipitation of the oxalates, carbonates, or acetates, followed by calcination. The co-precipitation method is preferred. Generally, the mixture of CuO and ZnO in the presence of the promoter metal is reduced by hydrogen of carbon monoxide at a temperature in the range of between 160° and 250° C. for several hours, preferably 8 to 24 hours.

The catalyst of the present invention can be used in a powder form or a tablet form obtained by compression molding. It can be employed in any reaction system such as a fixed bed system or a fluid bed system. After activation through hydrogenation according to the ordinary method, the catalyst is used in the hydrogenation reaction of the present invention.

The mixture of CuO and ZnO and the promoter is reduced prior to its use as catalyst in the aldehyde hydrogenation process. Hydrogen or carbon monoxide, or mixtures thereof, are used as the reducing agent. The hydrogen, carbon monoxide, or mixtures thereof, are generally mixed with an inert gas such as steam, nitrogen, or combustion gas, to maintain the catalyst bed temperature and to carry away the heat of reduction.

Reduction of the mixture of CuO and ZnO in presence of the promoter metal is complete when no more hydrogen is being reacted as shown by analysis of the inlet and outlet hydrogen. Complete reduction of the mixture occurs when the total amount of water produced in the reduction is equal to the stoichiometric value of water that should be produced when a given amount of copper oxide is reduced to copper. This value is about 36 gram of water per 450 gram of catalyst for a mixture of containing 35 weight percent of CuO.

The catalyst is generally formed into pellets, tablets, or any other suitable shape prior to use providing suitable surface area, by conventional techniques.

The process of the present invention is most conveniently carried out in batch operations although continuous or semi-continuous operations may also be employed.

Usually, an alcoholic medium such as ethanol or methanol as a reaction solvent is used in such an amount that the hydroxypivaldehyde or any other aldehyde concentration is within the range of 10 to 80% by weight, preferably 15 to 60% by weight. In case of hydroxypivaldehyde, if the concentration is more than 80% by weight, Tischenko reaction between the hydroxypivaldehydes themselves occurs, resulting in neopentylglycol ester of hydroxypivalic acid as by-product, which is unsuitable for practical use.

The hydrogenation can be carried out batchwise or continuously, advantageously at 100–200° C., preferably from 120–180° C., under a moderate pressure of from 20 psig to 500 psig, preferably from 400–500 psig. In a batchwise hydrogenation process, the catalyst is usually employed in an amount of from 2–12 percent by weight, preferably from 5–10 percent by weight, based on aldehyde, with a reaction time 1–4 hours, preferably 2–3 hours. According to the invention the catalyst is reduced with hydrogen at pressure of 300–500 psig, preferably 400–500 psig and at a temperature of 100–200° C., preferably 120–160° C., the solvent is alcohol, preferably methanol or ethanol, especially methanol and water mixture.

According to the invention the atomic ratios of the components in the catalyst is from 0.8–1.25 of copper and 1.5–2.5 of zinc, more preferably 1.0–1.1 of copper and 1.8–2.0 of zinc. Similarly, according to this invention the atomic ratios of copper to aluminium is 1.0–1.5 of copper, 0.75–1.20 of aluminium, more preferably, 1.20–1.40 of copper and 0.90–1.10 of aluminium.

The catalyst component used in the present invention is an environmental friendly, and easy to prepare and handle on an industrial scale. Furthermore, the presence of trialkylamines, formaldehyde will not deactivate this catalyst, and the hydrogenation can be carried out on crude hydroxypivaldehyde, thus avoiding the isolation and purification steps. According to this invention, even the presence of benzyl trimethylammonium hydroxide in the hydrogenation of hydroxypivaldehyde does not adversely affect the conversion of hydroxypivaldehyde, selectivity of the product neopentyl glycol and activity of the catalyst.

According to this inventions, the hydroxypivaldehyde conversion is 100%, and the selectivity of neopentyl glycol is also 100%, thus the desired product yield turns out to be quantitative and free from any unwanted impurity.

The process of the present invention is suitable for hydrogenating straight or branched aldehyde(s) containing the number of atoms or groups specified in Formula (I) and (III). These aldehydes include saturated aldehydes like acetaldehyde, propionaldehyde, isobutyraldehyde, n-butyraldehyde, isopentylaldehyde, n-pentyl aldehyde, 2-methyl pentyl aldehyde, crotonaldehyde, 2-ethyl hexaldehyde, methyl pentyl aldehyde, 2-ethyl butyraldehyde, and unsaturated $C_{3-8}$ aldehydes like acrolein, 2-ethyl propylacrolein, and benzaldehyde, furaldehyde, pyridinylaldehyde and the like. The aldehyde may be in a substantially pure state or admixed with a component(s) other than an aldehyde. Further, a mixture of aldehydes may be employed.

An oxo process or a cross-aldol condensation may obtain the aldehyde or mixture of aldehydes employed herein. A portion of the totality of the product mixture of an oxo process may be employed. Thus, the aldehyde(s) products or a portion of them may be separated from the product stream of an oxo process for hydrogenation by the process of this invention. For the purpose of providing an aldehyde feed, a conventional oxo product stream may be employed.

The aldehyde or mixture of aldehydes employed herein may also be obtained by processes other than oxo process, such as by oxidation of olefins or saturated hydrocarbons or by an aldol condensation.

The process of the present invention comprises contacting a liquid-phase solution of aldehyde(s) of Formula (I) and (III) and hydrogen alone or in admixture with other gases (desirably gases inert to the aldehyde and the catalyst), with a solid catalyst comprising a reduced mixture of CuO and ZnO in presence of a promoter like Aluminium or any other metal of Group III of the Periodic Table. The gaseous mixtures containing hydrogen include inert gases such as nitrogen, or carbon dioxide.

The term "hydrogen-containing gas" as used herein includes both substantially pure hydrogen gas as well as gaseous mixtures containing hydrogen.

The mole ratio of contained hydrogen gas to aldehyde(s) may be generally from 15 to 40 and preferably, from 20 to 30.

The hydrogenation process of the present invention is conducted at a temperature of between 110° and 180° C. preferably between 130° and 170° C. and at a pressure of between 20 and 500 psig, preferably between 400 and 500 psig.

The alcohol product from the hydrogenation reaction in the batch process is isolated from the reaction mixture using the conventional methods. The catalyst is filtered off and re-used for the next batch. The solvent from the filtrate is removed by a rotary evaporator. The recovered solvent is recycled in the next batch. The residual crude product is nearly pure, but is can be further purified by fractional distillation or fractional crystallization depending on the nature of the alcohol product.

The following examples are merely illustrative and are not presented as a definition of the limits of the invention.

EXAMPLE-1

Hydrogenation of Hydroxypivaldehyde

A 1.0 g quantity of the catalyst (CuO/ZnO/Aluminium oxide) in 50 ml methanol was placed in a 300 ml capacity Parr reactor. The contents were treated with hydrogen at 170° C., under pressure of 400–500 psig for 2–3 hrs. Cooled to room temperature, depressurized, followed by the addition of 10.0 g of hydroxypivaldehyde, in 50 ml methanol. Hydrogenation was carried out at 170° C., under a pressure of 400–500 psig, for 2–3 hrs. The conversion of hydroxypivaldehyde was 100% providing 100% selectivity of neopentyl glycol, the desired alcohol product.

EXAMPLE-2

Hydrogenaiton of Benzaldehyde

A 1.0 g quantity of the catalyst (CuO/ZnO/Aluminium oxide) in 50 ml methanol was placed in a 300 ml capacity Parr reactor. The contents were treated with hydrogen at 170° C., under pressure of 400–500 psig for 2–3 hrs. Cooled to room temperature, depressurized, followed by the addition of 10.0 g of benzaldehyde, in 50 ml of methanol. Hydrogenation was carried out at 170° C., under a pressure of 400–500 psig, for 2–3 hrs. The conversion of benzaldehyde was 100% providing 100% selectivity of benzyl alcohol, the desired alcohol product.

EXAMPLE-3

Hydrogenation of 4-Hydroxybenzaldehyde

A 1.0 g quantity of the catalyst (CuO/ZnO/Aluminium oxide) in 50 ml methanol was placed in a 300 ml capacity Parr reactor. The contents were treated with hydrogen at 170° C., under pressure of 400–500 psig for 2–3 hrs. Cooled to room temperature, depressurized, followed by the addition of 10.0 g of 4-hydroxybenzaldehyde, in 50 ml of methanol. Hydrogenation was carried out at 170° C., under a pressure of 400–500 psig, for 2–3 hrs. The conversion of benzaldehyde was 100% providing 100% selectivity of 4-hydroxybenzyl alcohol, the desired alcohol product.

EXAMPLE-4

Hydrogenation of Isobutyraldehyde

A 1.0 g quantity of the catalyst (CuO/ZnO/Aluminium oxide) in 50 ml of methanol was placed in a 300 ml capacity Parr reactor. The contents were treated with hydrogen at 170° C., under pressure of 400–500 psig for 2–3 hrs. Cooled to room temperature, depressurized, followed by the addition of 10.0 g of isobutyraldehyde, in 50 ml of methanol. Hydrogenation was carried out at 170° C., under a pressure of 400–500 psig, for 2–3 hrs. The conversion of isobutyraldehyde was 100% providing 100% selectivity of isobutyl alcohol, the desired alcohol product.

EXAMPLE-5

Hydrogenaiton of n-butyraldehyde

A 1.0 g quantity of the catalyst (CuO/ZnO/Aluminium oxide) in 50 ml of methanol was placed in a 300 ml capacity Parr reactor. The contents were treated with hydrogen at 170° C., under pressure of 400–500 psig for 2–3 hrs. Cooled to room temperature, depressurized, followed by the addition of 10.0 g of n-butyraldehyde, in 50 ml of methanol. Hydrogenation was carried out at 170° C., under a pressure of 400–500 psig, for 2–3 hrs. The conversion of n-butyraldehyde was 100% providing 100% selectivity of n-butyl alcohol, the desired alcohol product.

The features disclosed in the foregoing description or in the claims may, both separately and in any combination thereof, be material for realising the invention in diverse forms thereof.

What is claimed is:

1. A heterogeneous liquid-phase process for the catalytic hydrogenation of aldehydes to the corresponding alcohols wherein the process comprises reacting an aldehyde in alcoholic or aqueous-alcoholic solution with hydrogen gas in the presence of a catalyst comprising a reduced mixture of solid CuO/ZnO promoted by a metal of group IIIA in the Periodic Table, characterized in that the concentration of the aldehyde in the alcoholic or aqueous-alcoholic solution is within the range of 10 to 80% by weight when starting the process, and wherein the atomic ratio of copper to the metal group IIIA is 1.0–1.5:0.75–1.2.

2. The process according to claim 1 wherein the metal of group IIIA is aluminium.

3. The process according to claim 1 wherein the hydrogenation is carried out at a temperature of between 110° C. and 180° C. and a pressure of between 20 and 500 psig.

4. The process according to claim 2 wherein the hydrogenation is carried out at a temperature of between 110° C. and 180° C. and a pressure of between 20 and 500 psig.

5. The process according to claim 1 wherein said aldehyde is represented by formula (I) or formula (III):

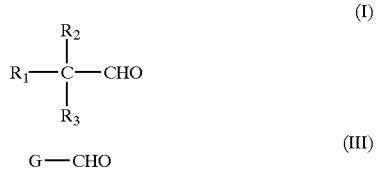

wherein $R_1$, $R_2$, and $R_3$ independently are straight chains or branched alkyl groups containing 1–18 carbon atoms, or straight alkyl groups containing 1–18 carbon atoms with one or more hetero atoms being interspersed, or alicyclic rings containing three or more carbon atoms, where the ring(s) may or may not contain hetero atoms, or wherein $R_1$, $R_2$, and $R_3$ together or alternately form an alicyclic or aromatic ring (rings), or wherein any one or more of the R groups contain one or more primary, secondary or tertiary alcohol group(s);

and wherein G is a substituted or unsubstituted and fused or isolated aromatic or heterocyclic ring (rings).

6. The process according to claim 4 wherein said aldehyde is represented by formula (I) or formula (III):

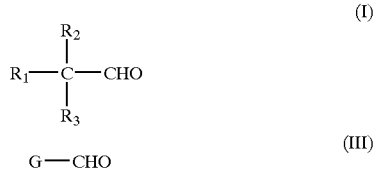

wherein $R_1$, $R_2$, and $R_3$ independently are straight chains or branched alkyl groups containing 1–18 or straight alkyl groups containing 1–18 carbon atoms with one or more hetero atoms being interspersed, or alicyclic rings containing three or more carbon atoms, where the ring(s) may or may not contain hetero atoms, or wherein $R_1$, $R_2$, and $R_3$ together or alternately form an alicyclic or aromatic ring (rings), or wherein any one or more of the R groups contain one or more primary, secondary or tertiary alcohol group(s);

and wherein G is a substituted or unsubstituted and fused or isolated aromatic or heterocyclic ring (rings).

7. The process according to claim 5 wherein G is a p-hydroxybenzyl group or a pyridinyl or furyl group.

8. The process according to claim 6 wherein G is a p-hydroxybenzyl group or a pyridinyl or furyl group.

9. The process according to claim 1, wherein said aldehyde is selected from the group comprising hydroxypivaldehyde, isobutyraldehyde, n-butyraldehyde, benzaldehyde and p-hydroxybenzaldehyde.

10. The process according to claim 4, wherein said aldehyde is selected from the group comprising hydroxypivaldehyde, isobutyraldehyde, n-butyraldehyde, benzaldehyde and p-hydroxybenzaldehyde.

11. The process according to claim 5, wherein said aldehyde is selected from the group comprising hydroxypivaldehyde, isobutyraldehyde, n-butyraldehyde, benzaldehyde and p-hydroxybenzaldehyde.

12. The process according to claim 9, wherein said aldehyde is hydroxypivaldehyde contaminated with either triethylamine or benzyltrimethyl/ethyl ammonium hydroxide.

13. The process according to claim 11 wherein said aldehyde is hydroxypivaldehyde contaminated with either triethylamine or benzyltrimethyl/ethyl ammonium hydroxide.

14. The process according to claim 9 wherein said aldehyde is hydroxypivaldehyde contaminated with either formaldehyde and/or isobutyraldehyde.

15. The process according to claim 11 wherein said aldehyde is hydroxypivaldehyde contaminated with either formaldehyde and/or isobutyraldehyde.

16. The process according to claim 1, wherein the atomic ratio of copper to zinc in said catalyst is 0.8–1.25:1.5–2.5.

17. The process according to claim 4, wherein the atomic ratio of copper to zinc in said catalyst is 0.8–1.25:1.5–2.5.

18. The process according to claim 5, wherein the atomic ratio of copper to zinc in said catalyst is 0.8–1.25:1.5–2.5.

19. The process according to claim 11, wherein the atomic ratio of copper to zinc in said catalyst is 0.8–1.25:1.5–2.5.

20. The process according to claim 13, wherein the atomic ratio of copper to zinc in said catalyst is 0.8–1.25:1.5–2.5.

21. The process according to claim 15, wherein the atomic ratio of copper to zinc in said catalyst is 0.8–1.25:1.5–2.5.

22. The process according to claim 1 wherein said alcoholic or aqueous-alcoholic solution comprises methanol, ethanol or a mixture of methanol and ethanol.

23. The process according to claim 6, wherein said alcoholic or aqueous-alcoholic solution comprises methanol, ethanol or a mixture of methanol and ethanol.

24. The process according to claim 11, wherein said alcoholic or aqueous-alcoholic solution comprises methanol, ethanol or a mixture of methanol and ethanol.

25. The process according to claim 13 wherein said alcoholic or aqueous-alcoholic solution comprises methanol, ethanol or a mixture of methanol and ethanol.

26. The process according to claim 15 wherein said alcoholic or aqueous-alcoholic solution comprises methanol, ethanol or a mixture of methanol and ethanol.

27. The process according to claim 20 wherein said alcoholic or aqueous-alcoholic solution comprises methanol, ethanol or a mixture of methanol and ethanol.

28. The process according to claim 21 wherein said alcoholic or aqueous-alcoholic solution comprises methanol, ethanol or a mixture of methanol and ethanol.

* * * * *